United States Patent
Webb et al.

(10) Patent No.: US 6,314,793 B1
(45) Date of Patent: Nov. 13, 2001

(54) TEST DEVICE FOR MEASURING CHEMICAL EMISSIONS

(75) Inventors: Michael Webb, Pine Valley, UT (US); Robert Lott, Palatine, IL (US)

(73) Assignee: Gas Research Institute, Chicago, IL (US)

( * ) Notice: Subject to any disclaimer, the term of this patent is extended or adjusted under 35 U.S.C. 154(b) by 0 days.

(21) Appl. No.: 09/407,389

(22) Filed: Sep. 28, 1999

(51) Int. Cl.[7] .............................. G01M 3/18; G01N 1/24; B01D 46/10

(52) U.S. Cl. ............................... 73/40.7; 73/40.5; 73/46; 73/861.85; 73/864.33; 422/68.1

(58) Field of Search .................................. 73/40.7, 40.5, 73/23.2, 30.03, 31.03, 46, 861.77, 861.85, 864.33; 422/68.1

(56) References Cited

U.S. PATENT DOCUMENTS

| | | | |
|---|---|---|---|
| 3,187,558 | | 6/1965 | Koncen et al. ...................... 73/24.03 |
| 3,246,968 | * | 4/1966 | Bailey ..................................... 48/193 |
| 3,618,061 | * | 11/1971 | Livers ................................... 340/236 |
| 3,786,675 | | 1/1974 | Delatorre et al. ..................... 73/40.7 |
| 3,987,662 | * | 10/1976 | Hara et al. ........................ 73/40.5 R |
| 4,177,673 | * | 12/1979 | Krueger ................................. 73/189 |
| 4,450,711 | * | 5/1984 | Claude ............................. 73/40.5 R |
| 4,573,344 | * | 3/1986 | Ezekoye .................................. 73/46 |
| 4,574,619 | * | 3/1986 | Castellant et al. .................... 73/40.7 |
| 4,715,213 | * | 12/1987 | McGreehan et al. ................. 73/40.7 |
| 4,726,824 | * | 2/1988 | Staten ..................................... 55/274 |
| 4,866,565 | | 9/1989 | Wray, Jr. .............................. 361/215 |
| 5,150,499 | | 9/1992 | Berfield ................................ 361/212 |
| 5,159,523 | | 10/1992 | Claassen et al. ..................... 361/215 |
| 5,206,818 | | 4/1993 | Speranza .......................... 73/23.2 X |
| 5,417,105 | * | 5/1995 | Martinez et al. ..................... 73/40.7 |
| 5,511,409 | * | 4/1996 | Knaebel ............................... 73/28.04 |
| 5,517,862 | * | 5/1996 | Berrong et al. .................... 73/861.85 |
| 5,563,335 | | 10/1996 | Howard ..................................... 73/46 |
| 6,189,369 | * | 2/2001 | Yokogi .................................. 73/40.7 |

OTHER PUBLICATIONS

Robert A. Lott, "1994 International Workshop Environmental and Economic Impacts of Natural Gas Losses", *Measuring Gas Leaks*, Mar. 22–24, 1994, Czech Republic.

Berglund, Ronald L., Wood, David A., Union Carbide Corporation, Continuous Monitoring of Ethylene Oxide Fugitive Emissions, Association Dedicated to Air Pollution Control and Hazardous Waste Management (APCA), New York, NY, Jun. 21–26 1987, pp. 5 and 16.

Chemical Manufacturers Association, Improving Air Quality: Guidance for Estimating Fugitive Emmisions from Equipment, Chemical Manufacturers Association, Washington DC, Jan. 1989.

(List continued on next page.)

*Primary Examiner*—Helen Kwok
*Assistant Examiner*—David J. Wiggins
(74) *Attorney, Agent, or Firm*—Pauley Peterson Kinne & Fejer

(57) ABSTRACT

A test device for measuring chemical emissions to the atmosphere from a leaking component that includes a housing containing an air mover for drawing ambient air directly into the housing. The air mover is capable of operating at a high flow rate and a low flow rate. A detector for detecting the presence of a chemical emission is positioned within the housing as well as a calculator for measuring the concentration of the chemical emission. Air is drawn directly into a housing at a low flow rate in a survey mode and once a leak is detected air is drawn directly into the housing at a high flow rate in a quantification mode. During the quantification mode the calculator determines a leak rate from the leaking component or alternatively indicates that the calculated leak rate is unreliable.

20 Claims, 1 Drawing Sheet

OTHER PUBLICATIONS

STAR Environmental, Torrance, California: *Laboratory Test And Field Test Report Of Star Environmental's High Volume Collection System (HVCS)*, prepared for Robert A. Lott for Gas Research Institute, Jan. 24, 1994 Draft.

William S. Eaton et al., *Experimental Techniques For The Determination Of Fugitive Hydrocarbon Emmissions*, Air Pollution Control Association, 71st Annual Meeting, Houston, Texas, Jun. 25–30, 1978, 78–36.5.

Rosebrook, Donald D., Wetherold, Robert G., Smith, Calvin D., Harris, Graham E., *The Measurement Of Fugitive Hydrocarbon Emissions From Selected Sources In Petroleum Refineries*, Air Pollution Control Association, 71st Annual Meeting of the Air Pollution Control Association, Houston, Texas, Jun. 25–30, 1978, 78–36.4.

American Petroleum Institute, Washington D.C.: *Volume II–Fugitive Hydrocarbon Emissions From Petroleum Production Operations*, API Publication No. 4322, Mar. 1980.

Berglund, Ronald L., Wood, David A.: Continuous Monitoring of Ethylene Oxide Fugitive Emissions, pp. 5 and 16, presented at the 80th Annual Meeting of Air Pollution Control and Hazardous Waste Management (APCA), New York, NY, Jun. 21–26 1987.

*Improving Air Quality: Guidance for Estimating Fugitive Emissions From Equipment*, Chemical Manufacturers Association, Washington, DC, Jan. 1989.

Theresa Hosick and Touché Howard: *Fundamental Uncertainties in Estimating Fugitive Emissions Using Screening Concentrations at Process Components*, Paper No. 39–G, prepared for presentation at 1993 AICHE National Summer Meeting, Seattle, Washington.

Star Environmental, Torrance, California: *Final Report, Fugitive Hydrocarbon Emissions*: Eastern Gas Wells, for Gas Research Institute, Contract No. 5093–254–2640, Jul. 1995.

Eric S. Ringler: *Evaluation of the High Volume Collection System (HVCS) for Quantifying Fugitive Organic Vapor Leaks*, prepared for Environmental Protection Agency, EPA–600/R–95–167, Nov. 1995.

Indaco Air Quality Services, Inc., *Methane Emissions From Natural Gas Customer Meters: Screening and Enclosure Studies*, Nov. 1, 1992.

W. Keifer, and J. Griebstein: *Quantification of Fugitive Emissions From Piping Components Using a Portable Infra–Red Analyzer*, Air & Waste Management Assn., 94–WA71.01, Jun. 19–24, 1994.

R. Ricks and G. Harris: *Comparison of Fugitive Emission Measurement Methods for Selected Studies From the 1970s Until the 1990s*, Air & Waste Management Assn., 94–WA71.05, Jun. 19–24, 1994.

\* cited by examiner

TEST DEVICE FOR MEASURING CHEMICAL EMISSIONS

BACKGROUND OF THE INVENTION

1. Field of the Invention

This invention relates to a test device for the detection and measurement of chemical emissions to the atmosphere.

2. Description of Related Art

Industrial components, especially in aging plants, are highly susceptible to gas leaks and the escape of chemical emissions to the atmosphere. As a result, leak detection and measurement is an important safety and cost-saving tool within industrial plants.

A common method that is still employed for detecting leaks is covering a suspect component in soapy water to identify the leak. Alternatively, "sniffer" devices that use a flame ionization detector (FID) or other sensor to detect leaking gas can be used to find and identify the presence of a leak. FIDs are of limited utility for components that are leaking heavily in that if the gas emissions exceed 90,000 ppm the FID "flames out" and must be reset. Neither of the above-described methods is capable of measuring the quantity of the gas emitted but only the concentration of the emitted gas in a plume. Because the concentration of the emitted gas varies significantly with speed and direction of wind, the angle of the probe, the distance of the probe from the leak, the geometry of the leaking component and the flow rate of the sample through the instrument, attempts to correlate the leak rate with the concentration have been unsuccessful. Studies have shown that the scatter in the correlation of leak rate and concentration is 3 to 4 orders of magnitude. Therefore, by using a concentration measurement to determine leak rate, the leak could be calculated at any number between 1 cf per day and 10,000 cf per day.

Early methods for quantification involved bagging a leak and sending the bagged specimen to an off-site lab for testing. This process was time consuming and therefore very expensive. Later, components were bagged and a semi-mobile test device analyzed the sample at the test site.

As taught in Howard, U.S. Pat. No. 5,563,335, a test device was later conceived that drew in an air sample through a sample hose at a high flow rate so as to capture the entire leak and thereupon analyze the concentration of gas emissions within the air sample. By measuring both the concentration in the sample and the concentration in the background air, measurement of the leak rate may be obtained.

SUMMARY OF THE INVENTION

It is one object of this invention to provide a test device wherein air is drawn directly into a housing without passing through a sample hose thereby reducing frictional losses and the possibility for static charge build-up.

It is another object of this invention to provide a test device that corrects for contaminants in the background air as well as for interference from other leaks.

It is still another object of this invention to provide a test device that functions as both a leak detector and a leak quantifier.

It is yet another object of this invention to provide a test device that requires a minimal amount of input from an operator to generate useable test data.

A test device for measuring chemical emissions to the atmosphere according to one preferred embodiment of this invention preferably includes a static resistant housing for portable containment of the components of this invention.

An air mover, such as a fan, is positioned within the housing or can be located on the person of the operator such as a belt or backpack and may be connected to the housing with a hose. The fan is arranged to draw ambient air directly into the housing. A spark-proof motor is connected to the air mover and capable of operation at two or more speeds. An anemometer is positioned within the housing, preferably downstream of the air mover, for detecting a flow rate of air through the housing, as generated by the air mover.

A sampling head for detecting the presence of a chemical emission is positioned in communication with the housing, preferably within the housing. The sampling head preferably comprises a mixing element and a detector.

A calculator is connected in communication with the anemometer and the sampling head and measures the concentration of the chemical emissions from the leaking component. The calculator preferably comprises a computer or logic board that calculates the leak rate of the chemical emissions from the leaking component based upon several pre-programmed parameters.

A signal indicator is also positioned with respect to the housing and indicates to the operator whether a leak is detected. Once a leak is detected, according to one preferred embodiment of this invention, the test device is switched from a survey mode for identifying the presence of a leak to a quantification mode for measuring the leak rate of the leak from the component.

The test device may also include one or more of a volume display showing the volume of air passing through the housing; a chemical display showing the chemical emission content of the air passing through the housing; a leak display showing the total chemical emission rate; and/or a mode display showing whether the test device is in a surveying mode or a quantifying mode.

Preferably, the test device is operated with the air mover set at a low flow rate during the survey mode. When the presence of a leaking component is detected, the test device is set to draw air directly into the housing at a high flow rate during the quantification mode. The calculator thereupon determines the leak rate from the concentration of the chemical emission drawn through the housing and the flow rate measured by the anemometer. The calculator changes the flow rate and then recalculates the leaks rate. The calculator then uses the two leak rate values in an internal algorithm to determine whether the calculated leak rate is accurate; whether the entire leak was captured; and/or the presence or absence of the chemical in the background air. The test device thereby signals whether the test result is sufficient or whether the test result is unreliable based upon the presence of interference from another leaking component, presence of the chemical in the background air or incomplete capture of the leak. If the test result is unreliable, based upon the signal received, the operator can run another test from a different location near the leaking component.

The calculator may also calculate concentration, flow rate and leak rate by manipulating the output of the test device by several pre-programmed calculation factors. The calculator may additionally convert output data to digital values and calculate average values over specified time periods. Further, the calculator may control the operation of the test device during an automatic mode and provide signals to the operator during all modes. Finally, the calculator may record the accumulated data in a data logger and allow the accumulated data to be downloaded to a computer, such as a PC.

BRIEF DESCRIPTION OF THE DRAWINGS

The above-mentioned and other features and objects of this invention will be better understood from the following detailed description taken in conjunction with the drawings wherein.

DESCRIPTION OF PREFERRED EMBODIMENTS

Figure 1:
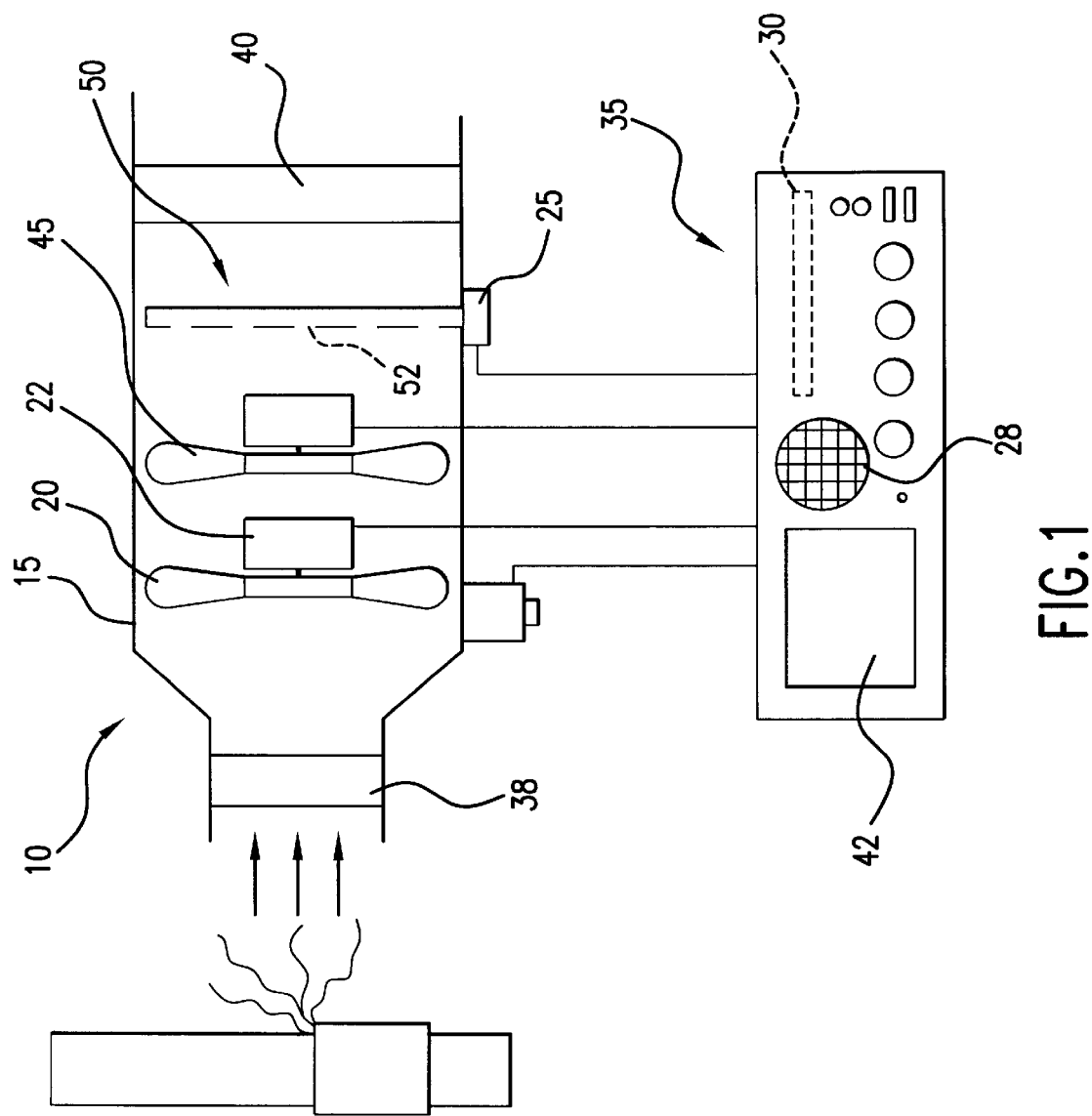
FIG. 1 is a schematic view of a test device according to one preferred embodiment of this invention.

FIG. 1 shows test device 10 for measuring chemical emissions to the atmosphere. Test device 10 includes housing 15 for containment of one or more important components of test device 10. Housing 15 is preferably manufactured from polyurethane or other conductive, static resistant, material known to those having ordinary skill in the art. Additionally, housing 15 is preferably portable and easily carried by an operator.

Air mover 20, such as fan or impeller, is positioned within housing 15 or attached to housing 15 with a hose (not shown). Air mover 20 is likewise preferably constructed from a static resistant material. Air mover 20 is arranged within housing 15 to draw ambient air directly into housing 15. Air mover 20 is preferably connected with respect to motor 22 and is preferably capable of operating in at least two speeds, a high flow rate and a low flow rate.

Motor 22 preferably comprises a brushless motor mechanically connected to air mover 20. A brushless motor reduces the risk of sparking and thus the potential for explosion in environments heavy in gas emissions. A bilge pump motor or other motor federally approved as explosion-proof may alternatively be employed.

Additionally, test device 10 according to one preferred embodiment of this invention further includes at least one flame arrester 40 positioned within housing 15, preferably at an inlet and/or outlet of housing 15. Flame arrester 40 may comprise a densely packed fiberous filter or other configuration that does not greatly impede air flow and yet prevents the passage of flames and/or sparks.

According to one preferred embodiment of this invention, test device 10 further comprises control unit 35 connected with respect to air mover 20 for adjusting the speed of air mover 20. The speed of air mover 20 may be input by the operator or automatically set by test device 10 depending upon known parameters. The speed of air mover 20 is controlled by varying either the voltage, current or frequency of the power sent from control unit 35 to motor 22.

According to one preferred embodiment of this invention, anemometer 45 is positioned within housing 15 for detecting a flow rate of air through the housing, as generated by air mover 20. Anemometer 45 is preferably, though not necessarily, positioned downstream with respect to air mover 20. According to one preferred embodiment, anemometer 45 comprises a plurality of rotating vanes positioned in between a light emitting diode and a light receiving diode. Anemometer 45 preferably produces an electric signal that varies as a function of the speed of rotation of anemometer 45.

Detector 25 for detecting the presence of a chemical emission is positioned in communication with housing 15, preferably within housing 15. Detector 25 preferably comprises a chemical sensing element. The type of chemical sensing element would vary with the chemical to be measured and the size of the leaks expected and comprises an appropriate chemical sensing element known to those having ordinary skill in the art.

Detector 25 is contained within sampling head 50 positioned within housing 15 and, preferably though not necessarily, downstream with respect to anemometer 45. In addition to detector 25/chemical sensing element, sampling head 50 also may include mixing element 52. Mixing element 52 is preferably a perforated manifold or other device for thoroughly mixing the air stream prior to sampling by the chemical sensing element. Although not shown in FIG. 1, detector 25 may alternatively be positioned outside of housing 15.

According to one preferred embodiment of this invention, calculator 30 is connected in communication with housing 15 for measuring the concentration of the chemical emissions. Calculator 30 receives signals from one or both of anemometer 45 for determining air flow rate and detector 25 within sampling head 50 for determining concentration of gas emissions. Calculator 30 preferably comprises a computer and/or logic board that calculates the leak rate of the chemical emissions from the leaking component based upon several pre-programmed parameters, controls the flow rate through test device 10 as well as other functions discussed in more detail hereinafter.

According to one preferred embodiment of this invention, signal indicator 28 is positioned with respect to housing 15 to indicate the presence of the chemical emission that exceeds a predetermined concentration. Signal indicator 28 may comprise an audible electronic signal transmitted to headphones, an audible signal transmitted directly from a speaker within housing 15 or a visual signal displayed on or in communication with housing 15. Such a signal indicator 28 permits an operator to identify the presence of a leak without concentrating on a steady stream flow of data shown in a monitor or other data display.

According to one preferred embodiment of this invention, test device 10 further comprises a volume display showing the volume of air passing through housing 15. Additionally, test device 10 may comprise a chemical display showing the chemical emission content of the air passing through housing 15. One or both of a leak display showing the total chemical emission rate and a mode display showing whether the test device is in a surveying mode or a quantifying mode may also be present on test device 10.

In operation, housing 15 is positioned adjacent to a leaking or potentially leaking component. Air is drawn into housing 15 by an electrically driven air mover 20, such as a fan. As the air moves through housing 15, the air causes a wind sensing anemometer 45 to rotate. A signal corresponding with the air flow through housing 15 is preferably sent to calculator 30. The air then passes across detector 25 to determine the amount of chemical in the air stream. The air then exits housing 15, in one preferred embodiment through filter 38 and/or flame arrester 40.

According to one preferred method of operation of this invention, test device 10 is operated with air mover 20 set at a low flow rate during a survey mode. When the presence of a leaking component is detected, test device 10 begins, either manually or automatically, drawing air directly into housing 15 at a high flow rate during a quantification mode. Calculator 30 thereupon determines the concentration of the chemical emission drawn through housing 15. Because the high flow rate of air drawn through housing 15 captures the entire leak from the leaking component, the concentration or leak rate from the component may be determined with great accuracy.

Calculator 30 preferably generates a test result upon determining the concentration of the leak and/or the leak rate from the leaking component. According to one preferred embodiment of this invention, calculator 30 will use an internal algorithm to determine whether the calculated leak rate is accurate; whether the entire leak was captured; and/or the presence or absence of background air in the calculation. Calculator 30 preferably signals whether the test result is sufficient or whether the test result is unreliable based upon the presence of interference from another leaking component and/or background air. In a preferred embodiment of this invention, test device 10 signals if interference is present in the test result. If interference or background air is present in the test result than, based upon the signal received, the operator can run another test from a different location near the leaking component. Alternatively, the algorithm within calculator 30 will determine and adjust air mover 20 to an appropriate flow rate that will capture the entire leak.

According to one preferred embodiment of this invention, as the operator progresses in a survey mode, the operator would observe a concentration above a threshold level or be alerted by an audible signal and then actively switch to a test mode where the leak rate is determined. A computer or other data gathering device can be connected with respect to calculator 30 to compile and manipulate leak data into a tabulated, organized format.

Calculator 30, motor 22, display devices and any other component requiring power are preferably connected to a battery, such as a solid state lithium battery. Weight, battery life and leak resistance are all important factors relative to the selection of an appropriate power supply and/or battery.

Operation of the Test Device

According to this invention, test device 10 may be operable in many different configurations. The following description is for illustration purposes only and does not encompass the only method of operation of test device 10, only one preferred method of operation.

According to one preferred embodiment of this invention, the following inputs are contained in test device 10. The pre-set values of test device 10 preferably include: date; time; calibration flow rate (FRcal); maximum flow rate (FR max); second flow rate (FR2); screening flow rate (FRscreen); minimum concentration (Cmin); maximum concentration (Cmax); concentration alarm threshold (Calarm); error limits (1 and 2); anemometer calibration constants; and/or detector calibration constant.

The following inputs are preferably input during operation of test device 10: title information; ID number; concentration alarm threshold (C alarm); maximum flow rate (FR max); test number (TEST#) when data is designated for deletion.

A touch pad or other appropriate input device can be used to enter the above-described inputs into test device 10. The touch pad may include numbers, letters and/or special keys such as identification number (ID); an ENTER key to enter values; a CALIBRATE key for calibration of anemometer 45; an OvRid key to override "bad" signals or data and record with a flag; a TEST # key to input test number to identify data to be deleted; a BG key to input background value in MANUAL mode or to execute the background calculation in the automatic mode.

Test device 10 preferably further includes one or more of the following switches for operation: SURVEY/SCREEN switch to enter the survey mode; a MANUAL switch for entering a manual mode; an AUTO switch for entering an automatic mode; TAKE DATA/QUANTIFICATION switch to signal test device 10 to take data; DELETE switch to delete recorded data.

As an initial matter, test device 10 is preferably calibrated. Preferably, test device is calibrated with a standard calibration gas at two concentrations. The first concentration should be at a level that is expected for most measurements, typically this has been in the range of 2 to 10 percent. The second concentration should be at the maximum concentration of detector 25. A two way switch or valve on test device should be turned from "test" to "calibrate".

The calibration gas is preferably injected through a calibration port. A gain of test device 10 is adjusted so that the correct concentration appears on the display and the proper calibration is "locked-in" according to the operation of test device 10.

Another step in calibration of test device 10 is calibrating the flow rate. Test device 10 is first turned on and a key marked "MANUAL" is depressed followed by a "CALIBRATE" key. The flow rate through test device 10 will automatically be set at the calibration value of XX cfm (i.e., FR=$FR_{cal}$=XX cfm). A flow rate meter is attached to test device and two calibration values are manually recorded. A gain of anemometer 45 is appropriately adjusted and "locked-in" according to the procedures of operation of test device 10.

Following calibration, test device 10 is preferably used to screen for leaks. A "SCREEN" key is preferably depressed to engage the survey mode. Next, an alarm threshold to activate signal indicator 28 is set to a default value, such as 50 ppm. This may be accomplished with a series of keystrokes such as a "0" key then the "ENTER" key. A different alarm threshold value may be assigned by depressing the "SCREEN" key followed by the number on the touch pad corresponding to the desired level in ppm and the "ENTER" key. For example, the flow rate (FR) will be set at the screening value of 0.2 cfm (i.e., FR=FRscreen) and the instrument will alarm when the concentration exceeds the threshold which is 50 PPM for the default case (i.e., C=Calarm=50 PPM)

Following calibration, test device 10 may be operated in a manual mode. According to one preferred embodiment of this invention, test device 10 is switched to MANUAL then the "0" key is depressed followed by the ENTER key to set the flow rate (FR) to the default value of 10 cfm (FR=FRmax=10 cfm). To set the flow rate to a different value press "MANUAL" then enter the desired value in cfm using the touch pad and press "ENTER".

Next, press the "ID" key to enter the component identification number that will identify the component to be tested. Enter as many as 10 digits and then press ENTER.

According to one preferred embodiment of this invention, test device 10 will start cycling over a period, 9 seconds for example, in which it will take data at a rate of XX/sec and calculate 3 and 9 second average values of concentration (C), flow rate (FR), and leak rate (LR). During this time the instrument will preferably display 3 second average values of either leak rate or concentration at 3 second intervals.

When the test device is properly positioned at the leak and checks have been made to: a) insure that the leak is sheltered from high winds; b) there is not any interference from other nearby leaks; and c) the background concentration is low, the "TAKE DATA" button on test device 10 is depressed. Test device 10 will record average values of flow rate, concentration, and leak rate at equal intervals, such as every 9 seconds. The system will assign a test number for each test performed for each component "ID". Multiple data points can be record by press "TAKE DATA" successively.

If the background concentration is determined to be large, the "BG" key is depressed and the background concentration in ppm is entered using the touch pad followed by the ENTER key. Then the "ID" key is used followed by entry of the identification number of the component with the high background value. All data collected after this point with the same "ID" will use the background concentration in the leak rate calculation. To take additional data for the same component (i.e., same "ID" number), the "TAKE DATA" key is depressed. A "TEST #" will be assigned to each test point sequentially and automatically.

The "DELETE" button on test device 10 is used to delete data just recorded at which point a prompt on test device 10 will display "DELETE?" which is confirmed by pressing "DELETE" again. To delete a data record before the last data point, the "ID" key is used followed by entry of the relevant ID number and the ENTER key. The "TEST #" is used to enter the test number followed by "ENTER" and "DELETE." For example, to delete the data for the third test of component 132, the progression would require the ID key followed by "132" and then "TEST #," "3" and finally "DELETE." To measure other components press "ID" and enter the component ID number, press ENTER and repeat the above procedure.

Test device 10 may also be operated in an automatic mode. After calibrating test device 10, the "AUTO" switch is selected. When test device 10 is positioned properly at a leak and sufficient checks are made to determine that (a) the leak is shielded from high winds, (b) interference from nearby leaks are not a problem, and (c) the background concentration is sufficiently low, the "ID" is pressed followed by entry of the component ID number through the touch pad and the ENTER key.

The "TAKE DATA" is next depressed at which point calculator 30 will automatically take data at two flow rates and compare the values and perform appropriate internal analysis to determine whether the acquired data is acceptable. The user is then provided a messages on the status of the test. If the data are good then the data points are stored. The operator can take additional data points for the same component by pressing "TAKE DATA". To measure leakage from another component an new "ID" number must be entered as described above. To continue screening the facility for leaks just press "SCREEN", then 0 and ENTER.

The operator can receive a number of messages that indicates that the data is bad or suspect. First, according to one preferred embodiment of this invention, test device 10 will check to determine if the concentration was near a million ppm or the maximum value of the sensor (Cmax), indicating that test device 10 could not capture the entire leak and the data are bad. If the data are suspect or bad, test device 10 will alert the user such as by flashing 99999 on the display. Next, the concentration is checked to determine if it is below the minimum level (if C<Cmin). If the concentration is below the minimum level, the flow rate for the first data point (F1) is reset by calculating the new value as F1=C/Cmin*FR max. The second data point is then taken at a flow rate 15 percent lower then F1. This calculation is automatically performed by calculator and/or software within test device 10. The only indication the concentration is below the minimum level is that the flow rate displayed will be below the maximum value. Test device will then check to make sure the two data points are sufficiently close to the same value. If sufficiently close, the data are good and will be recorded. The operator will receive green light signals under "Good Data" and "Data Recorded".

If the data do not pass the automatic checks the operator will receive red light signals. In this case, the operator needs to take action as described below and re-test the component. However, the operator can override the software at this point and record the data by pressing "OvRid". The data will be flagged as "bad" and recorded.

The data could be bad for at least the three following reasons: 1) the leak was not completely captured; 2) there was interference from another leak; or 3) there is a large background concentration. Incomplete capture can result if the leak is too large or high winds surround the component and/or test device 10. A concentration near the maximum value of detector 25 is an indication that the leak is too large. However, if the concentration is not near the maximum, then the component needs to be shielded from the wind and the input of test device 10 needs to be positioned down wind from the leak and the test repeated. The possible occurrence of interference can be checked by the operator by screening components in the vicinity of the component being tested. If interference is detected the input of test device 10 should be located upstream of the interfering leak and the leak being tested should be shielded from the interfering component.

If the background is found to be large, the operator has two choices. The first is to press the "BG" key followed by "TAKE DATA". The instrument will then collect data over multiple flow rates, for example six flow rates, and will calculate the background concentration and apply this value to the first two data points. Test device 10 will then apply the data checks, determine if the data are "good" and record the values. The second approach is to perform the test in the "MANUAL" mode. In the MANUAL mode the background concentration is entered directly.

While in the foregoing specification this invention has been described in relation to certain preferred embodiments thereof, and many details have been set forth for purpose of illustration, it will be apparent to those skilled in the art that the test device according to this invention is susceptible to additional embodiments and that certain of the details described herein can be varied considerably without departing from the basic principles of the invention.

We claim:

1. A test device for measuring chemical emissions to the atmosphere, the test device comprising:
   a housing;
   an air mover positioned within the housing for drawing ambient air directly into the housing, the air mover operating at a high flow rate and a low flow rate;
   an anemometer positioned within the housing;
   a detector for detecting the presence of a chemical emission in communication with the housing;
   an output device viewably positioned with respect to the test device, the output device displaying at least one of a flow rate and a concentration of chemical emissions; and
   at least one flame arrester positioned within the housing.

2. The test device of claim 1 further comprising a recorder in communication with the test device to record at least one of a flow rate and a concentration of chemical emissions.

3. The test device of claim 1 further comprising a calculator in communication with the housing for determining a leak rate of the chemical emission.

4. The test device of claim 1 further comprising a signal indicating that a test result is inadequate.

5. The test device of claim 1 further comprising a control unit connected with respect to the air mover, the control unit for adjusting the speed of the air mover.

6. The test device of claim 1 further comprising an audible signal indicator positioned with respect to the housing to indicate the presence of the chemical emission.

7. The test device of claim 1 further comprising a brushless motor mechanically connected to the air mover.

8. The test device of claim 1 further comprising a switch for transferring the test device from a survey mode to a quantification mode.

9. A test device for measuring chemical emissions to the atmosphere, the test device comprising:

a housing;

a fan positioned within the housing;

an anemometer positioned within the housing and downstream with respect to the fan;

a sampling head positioned within the housing and downstream with respect to the anemometer, wherein the sampling head comprises a mixing device and a chemical sensing element; and a calculator electrically connected with respect to the housing for calculating a leak rate of the chemical emissions based upon a flow rate from the anemometer and a concentration of the chemical emissions from the sampling head.

10. The test device of claim 9 wherein the calculator further comprises:

a volume display showing the volume of air passing through the housing;

a chemical display showing the chemical emission content of the air passing through the housing; and a leak display showing the total chemical emission rate.

11. A test device for measuring chemical emissions to the atmosphere, the test device comprising:

a housing;

a fan positioned within the housing;

an anemometer positioned within the housing and downstream with respect to the fan;

a sampling head positioned within the housing and downstream with respect to the anemometer; and a calculator electrically connected with respect to the housing for calculating a leak rate of the chemical emissions based upon a flow rate from the anemometer and a concentration of the chemical emissions from the sampling head, the calculator including:

a volume display showing the volume of air passing through the housing;

a chemical display showing the chemical emission content of the air passing through the housing;

a leak display showing the total chemical emission rate; and a mode display showing whether the test device is in a surveying mode or a quantification mode.

12. A test device for measuring chemical emissions to the atmosphere, the test device comprising:

a housing constructed from a static dissipating material;

a fan positioned within the housing;

an anemometer positioned within the housing and downstream with respect to the fan;

a sampling head positioned within the housing and downstream with respect to the anemometer; and a calculator electrically connected with respect to the housing for calculating a leak rate of the chemical emissions based upon a flow rate from the anemometer and a concentration of the chemical emissions from the sampling head.

13. A test device for measuring chemical emissions to the atmosphere, the test device comprising:

a housing;

an air mover positioned with respect to the housing for drawing ambient air directly into the housing, the air mover operating at a high flow rate and a low flow rate, wherein the air mover is positioned within a backpack, the backpack connected with respect to the housing through a hose;

an anemometer positioned within the housing;

a detector for detecting the presence of a chemical emission in communication with the housing; and a calculator in communication with the housing for determining a leak rate of the chemical emission.

14. A test device for measuring chemical emissions to the atmosphere, the test device comprising:

a housing;

an air mover positioned within the housing for drawing ambient air directly into the housing, the air mover operating at a high flow rate and a low flow rate;

an anemometer positioned within the housing;

a detector for detecting the presence of a chemical emission in communication with the housing;

an output device viewably positioned with respect to the test device, the output device displaying at least one of a flow rate and a concentration of chemical emissions; and a switch for transferring the test device from a survey mode to a quantification mode.

15. The test device of claim 14 further comprising a recorder in communication with the test device to record at least one of a flow rate and a concentration of chemical emissions.

16. The test device of claim 14 further comprising a calculator in communication with the housing for determining a leak rate of the chemical emission.

17. The test device of claim 14 further comprising a signal indicating that a test result is inadequate.

18. The test device of claim 14 further comprising a control unit connected with respect to the air mover, the control unit for adjusting the speed of the air mover.

19. The test device of claim 14 further comprising an audible signal indicator positioned with respect to the housing to indicate the presence of the chemical emission.

20. The test device of claim 14 further comprising a brushless motor mechanically connected to the air mover.

* * * * *